United States Patent [19]

Schnur et al.

[11] Patent Number: 5,077,085
[45] Date of Patent: Dec. 31, 1991

[54] HIGH RESOLUTION METAL PATTERNING OF ULTRA-THIN FILMS ON SOLID SUBSTRATES

[76] Inventors: Joel M. Schnur, 6009 Lincolnwood Ct., Burke, Va. 22015; Paul E. Schoen, 5006 Taney Ave., Alexandria, Va. 22304; Martin C. Peckerar, 12917 Buccaneer Rd., Silver Spring, Md. 20904; Christie R. K. Marrian, 6805 Kenyon Dr., Alexandria, Va. 22307; Jeffrey M. Calvert, 6033 Wilmington Dr., Burke, Va. 22015; Jacque H. Georger, Jr., 8409 Great Lake Rd., Springfield, Va. 22153

[21] Appl. No.: 22,439

[22] Filed: Mar. 6, 1987

[51] Int. Cl.$^5$ ............................................. B05D 5/12
[52] U.S. Cl. .................................. 427/98; 427/54.1; 427/58
[58] Field of Search .................. 427/98, 58, 54.1

[56] References Cited

U.S. PATENT DOCUMENTS

| | | | |
|---|---|---|---|
| 3,884,704 | 5/1975 | Rantell | 427/98 |
| 4,199,649 | 4/1980 | Yundt | 427/96 |
| 4,539,061 | 9/1985 | Sagiv | 427/407.1 |
| 4,587,203 | 5/1986 | Brault | 427/54.1 |
| 4,661,372 | 4/1987 | Mance | 427/54.1 |

FOREIGN PATENT DOCUMENTS 2144653A 3/1985 United Kingdom .................. 427/58

OTHER PUBLICATIONS

R. H. Tredgold and G. W. Smith, "Formed by Adsorption and by the Langmuir-Blodgett Technique", IEE Proc. vol. 129, pt. I, No. 4, Aug. 1984, pp. 137-140.

Primary Examiner—Peter A. Nelson
Attorney, Agent, or Firm—Wolf, Greenfield & Sacks

[57] ABSTRACT

A process for producing metal plated paths on a solid substrate of the kind which has polar functional groups at its surface utilizes a self-assembling monomolecular film that is chemically adsorbed on the substrate's surface. The solid substrate may, for example, be an insulator of the kind used for substrates in printed circuitry or may, as another example, be a semiconductor of the kind used in semiconductor microcircuitry. The chemical reactivity in regions of the ultra-thin film is altered to produce a desired pattern in the film. A catalytic precursor which adheres only to those regions of the film having enough reactivity to bind the catalyst is applied to the film's surface. The catalyst coated structure is then immersed in an electrolers plating bath where metal plates onto the regions activated by the catalyst.

12 Claims, 1 Drawing Sheet

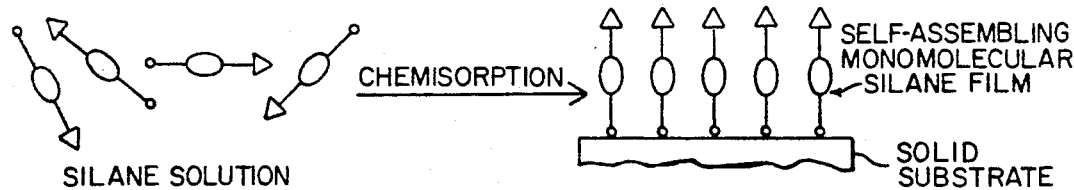
Fig. 1A
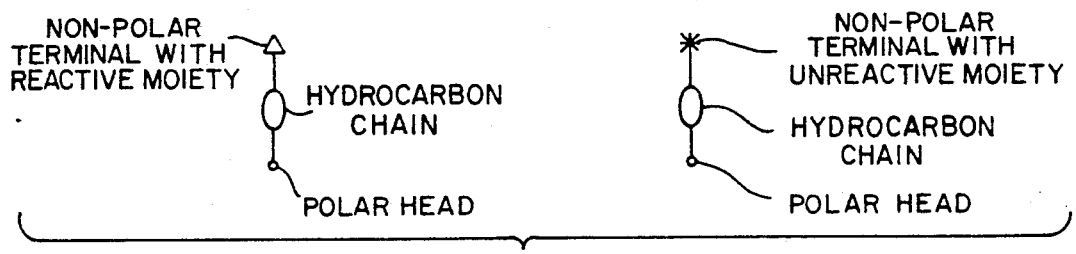
Fig. 1B
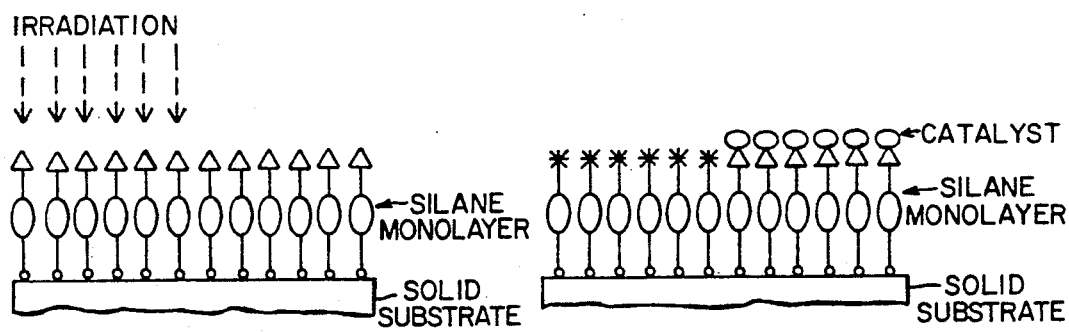
Fig. 2   Fig. 3
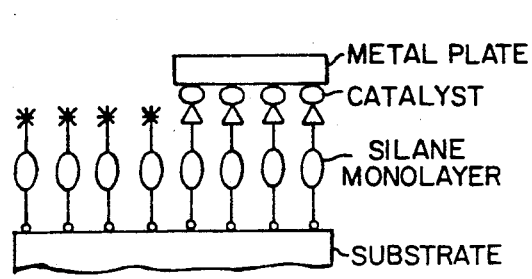 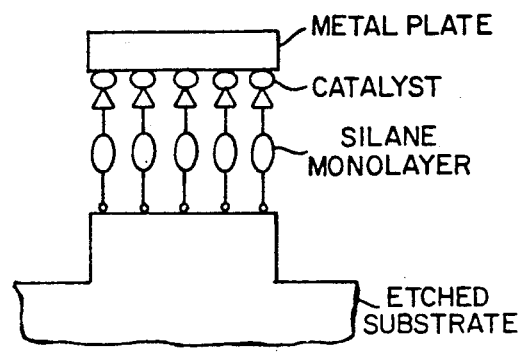
Fig. 4   Fig. 5

HIGH RESOLUTION METAL PATTERNING OF ULTRA-THIN FILMS ON SOLID SUBSTRATES

U.S. GOVERNMENT RIGHTS IN THE INVENTION

This invention was made jointly by four employees of the Naval Research Laboratory, Washington, D.C. and two employees of Geo-Centers, Inc. The two Geo-Centers employees, at the time the invention was made, were in the performance of work under Naval Research Laboratory contract N00014-85-C-2243. The United States of America has certain rights in the invention arising out of that contract, including a nonexclusive, nontransferable, irrevocable, paid-up license to practice the invention or have it practiced for or on behalf of the United States throughout the world. The United States of America may also have rights in the invention derived from the four employees of the Naval Research Laboratory who are joint inventors of this invention.

FIELD OF THE INVENTION

This invention relates in general to the production of ultra-thin films. More particularly, the invention pertains to self-assembling ultra-thin films that provide desired surface characteristics on substrates to which the films are strongly adherent. Yet even more particularly, the invention concerns procedures whereby areas of widely varying reactivity can be created with sub-micron lateral resolution on the substrate's surface. The invention enables the deposition of patterned thin metal coatings on semiconductor surfaces as a direct consequence of the differential reactivity.

The ability to spatially tailor surface chemical properties has significant applications in the field of microelectronics. The invention is particularly useful for the fabrication high-resolution resists, masks, and conductive paths that are essential to the production of integrated semiconductor devices. The invention is also useful for the production of high-resolution conductive paths on insulating substrates for printed circuits such as quartz, alumina, and organic polymers.

Although the deposition of metal on substrates in selected areas (commonly referred to as "selective patterning" or "selective deposition") relates to the making of both printed circuits and integrated circuits, the resolution requirements are sufficiently different that the two technologies will be treated separately herein.

BACKGROUND OF THE INVENTION

In Relation to Semiconductor Microlithography

Ongoing efforts to produce computers of higher speed at lower cost has led to the search for more efficient methods of fabricating high-resolution, high-density integrated circuitry on semiconducting substrates such as doped silicon and gallium arsenide. One aspect of that search is the investigation of methods for producing patterns of high resolution, i.e., patterns having line widths of less that one micron (a micron is one millionth of a meter), an area of research known as microcircuit lithography. For a detailed description of this subject, see the book entitled "Introduction to Microlithography", L. F. Thompson, C. G. Willson, and J. J. Bowden, editors, ACS Press, N.Y. (1983). At the present rate of miniaturization of integrated circuitry, it is anticipated that a resolution of approximately one quarter of a micron (i.e. 0.25 u) will be required within the next decade. For a discussion of the current state of the art in microlithography and an assessment of future requirements, see the monograph entitled, "The Submicron Lithography Labyrinth", A. N. Broers, Solid State Technology, June 1985, pp. 119 to 126.

In conventional fabrication of integrated circuits, patterning of the semiconductor surface is accomplished using the following general procedure. A radiation-sensitive organic coating (a "resist") is applied to the wafer surface. Prior treatment of the wafer with an adhesion-promoter such as hexamethyldisilazane (HMDS) is often employed. The coated surface is exposed to patterned radiation such as light, electron beams, gamma rays or X-rays. Exposure is made either by the "flood" or by the "scanning beam" technique. In flood irradiation, all the regions to be irradiated are exposed simultaneously. Patterned radiation is achieved either by projecting an image onto the substrate or by interposing a mask between the light source and the substrate. In the beam technique, the work is broken into small regions, or "pixels" that are exposed sequentially, generally by causing the beam to trace out the desired pattern. A "positive" resist material is one in which the irradiated region becomes more soluble, for example, by photo-induced bond scission. A "negative" resist material is one in which the irradiated region becomes less soluble, generally due to a free-radical polymerization reaction. Chemical development (e.g., exposure to concentrated sodium hydroxide or chlorinated hydrocarbon solvent) leaves behind a pattern of insoluble organic material. Exposure to an ion plasma or etchant solution removes substrate material in the uncovered areas. Residual organic material is chemically stripped, revealing the etched "troughs" and the unetched "plateau" regions that were protected by the resist.

Some of the prime considerations in the commercial production of integrated microelectronic circuitry are: resolution of the features in the semiconductor substrate; throughput; uniformity and reproducibility; and capital equipment and materials cost. Beam lithographic techniques that involve irradiation with electrons, ions, X-rays, gamma rays, or ultraviolet (UV) are known to offer resolution of features in the organic resist layer of well below one micron. For example, 0.4 micron features have been produced in poly(methylmethacrylate) (PMMA) using sub-200 nm (a nanometer is one thousandth of a micron or one billionth of a meter) UV irradiation from an excimer laser (D. Ehrich, et. al., J. Vac. Sci., 1985). Electron beam irradiation of multilayer films of vinyl stearate and w-tricosenoic acid, deposited using the Langmuir-Blodgett technique, has produced 60 nm wide lines and spaces (see: A. Barraud, et. Al., Thin Solid Films, 68, 1980, pp.91–100; also, A. Broers and M. Pomerantz, Thin Solid Films, 99, 1983, pp. 323–329).

A number of drawbacks exist with beam lithographic techniques. First, computer-controlled beam systems require considerable capital expenditure and are expensive to maintain. Second, the sequential irradiation of individual pixels is far more time-consuming than flood irradiation techniques. Throughput considerations (i.e., the time required to produce the item) take on greater significance as feature density and wafer size both continue to increase. Third, there is a tradeoff between resolution in the resist and etch resistance. It is known that the energy lost by electrons beamed into a solid is scattered in an oblong pear-shaped volume of diameter roughly equal to the electron penetration depth. The penetration depth increases with the energy of the incident electrons. Consequently, the diameter of the exposed area is at a minimum when the penetration depth is equal to the film thickness (positing the requirement that the entire thickness of the film be irradiated). Therefore, a means of obtaining improved resolution is by use of a thinner resist film, such as spin-cast organic polymer films or the Langmuir-Blodgett films described previously. However, ultra-thin organic film resists suffer from a number of problems that include film inhomogeneity (particularly pinholes) and the inability to withstand the vigorous plasma etching processes used to transfer the features of the resist to the underlying substrate.

Optical flood lithographic processes are the most widely employed because they offer the best combination of resolution and throughput. At the present time, the limit of resolution of microcircuitry features that can be produced on a scale practical for commercial production is on the order of one micron. Optical lithography generally involves patterned UV (sub-400 nm) irradiation of semiconductor substrates coated with a spin-cast organic resist film that is usually 300 nm to one micron thick. Principal limitations to attainment of higher resolution are due to a combination of the wavelength of light employed, the film composition, and thickness.

In optical lithography, it is known that resolution varies inversely with the wavelength of the irradiation. Therefore, high resolution is achieved by using radiation of the shortest possible wavelength to which the resist is sensitive. A number of light sources suitable for UV irradiation are available, including mercury lamps, xenon lamps, Nd-YAG lasers, excimer lasers, and fourth harmonic generation. Most of the high resolution photopolymeric resists that are now available are sensitive to near-UV (i.e., 320 to 400 nm) light. Few, if any photoresists are sensitive in the deep-UV (200 to 320 nm) or the vacuum-UV (below 200 nm) regions.

The wave length of ultraviolet radiation is in the 4 to 400 nm range. That range is loosely divided into near-UV (400 to 300 nm), far-UV (300 to 200 nm), and extreme-UV (below 200 nm). Extreme-UV radiation is strongly absorbed by air and therefore extreme-UV is usually used in evacuated apparatus. For that reason, extreme-UV is often refered to as "vacuum-UV".

As discussed above for beam techniques, the spin-coated resist films used in optical lithography must be at least several tenths of a micron thick to avoid pinholes and provide adequate resistance to plasma etching. Other limitations to resolution arise with the use of thick films due to defocussing of the image in the film, the occurrence of standing waves in the film, Rayleigh scattering from film inhomogeneities and from reduced control of the spatial extent of photoreactions. Spin coating tends to produce films that are thicker at the edges than in the center. Variations in the thickness of the film causes loss of resolution during contact mask exposure (i.e., where a patterned mask is in direct contact with the resist-coated substrate). Additionally, spin-coating machines are expensive and the substrates must be coated serially (i.e., one after the other).

Once patterned conventional optical resists generally require chemical development of the image (i.e., removal of the soluble resist material). Solvents employed in development, especially chlorinated hydrocarbons, are known to be environmentally hazardous. Resolution degradation is also induced during development by imperfect dissolution of the resist Other difficulties encountered with known resist films include imperfect or weak adhesion to the substrate, which can render the piece of work useless if needed resist regions come loose from the substrate. Resist materials often require special care in handling due to their sensitivity to ambient light, moisture and temperature.

Fabrication of conductive paths on a semiconductor substrate can be accomplished in a number of ways Generally, a thin metal coating is applied by vapor or sputter deposition over the entire area of the substrate. Most of the metal is removed in a later step following patterning and development steps. No flood optical lithographic process currently exists whereby high resolution metal patterns can be selectively deposited.

OBJECTS OF THE INVENTION

In Relation To Semiconductor Microcircuitry

The principal object of the invention with respect to the technology of semiconductor microcircuitry is to provide an ultra-thin high resolution resist film that can be patterned by irradiation with an electron beam or by irradiation with light whose wavelength is less than the 320 or 400 nm wavelength of the conventionally employed near-UV light, that does not require chemical development, that is pinhole-free, that is strongly adherent to the semiconductor substrate, that is more tolerant of varying environmental conditions than conventional resists and that retains its integrity under conditions of long exposure (i.e. many minutes) to the reactive ion plasmas now used in fabricating semiconductor microcircuits. In short, the principal objective of the invention is to provide an ultra-thin high resolution resist that does not have the drawbacks associated with the high resolution resists heretofore used in the fabrication of semiconductor microcircuits.

Another object of the invention is to provide a method of making microcircuits using conventional electroless plating technology to produce high resolution patterns on semiconductor substrates.

A further object of the invention is to provide an ultra-thin high resolution, strongly adherent, etch-impervious, positive resist pattern on a semiconductor substrate.

Yet another object of the invention is to provide a method of making microcircuits using standard wet chemistry techniques that avoid the need for complicated or expensive equipment such as the vacuum systems employed in some of the microcircuit fabricating methods now in use.

Another object of the invention is to produce an ultra-thin high resolution resist that remains stable over a wide temperature range and is sufficiently tolerant of high humidity so that specialized atmospheric control equipment is not needed for the protection of the resist.

BACKGROUND OF THE INVENTION

In Relation To Printed Circuitry

In the fabrication of printed circuits, adherent metal patterns are produced on insulative substrates such as organic polymers (e.g., acrylonitrile-butadiene-styrene or polysulfone) and metal oxides (e.g., aluminum oxide). As in the case of semiconductor substrates, metal patterns are generally formed by vapor deposition followed by patterning and removal of most of the metal layer.

A variety of procedures are known for the selective deposition of metal initially in only the desired areas of the substrate. In one such procedure employed with a polymeric substrate, a patterned photoresist layer is etched by an acid and the etched resist surface is then activated for metal deposition by exposure to a solution of tin salts and noble metal salts which are applied consecutively or are applied jointly as a mixture. After activation of the etched surface, the substrate is immersed in an electroless plating bath. A typical electroless plating bath contains metal ions, complexing agents, stabilizers and a reducing agent. The reducing agent causes the complexed metal ions to be reduced to metal only in the activated regions. The plated metal surface is itself catalytic for further metal deposition, thus the thickness of the plated layer can be varied by regulating the length of time in which the substrate is immersed in the plating bath. For a report on the technical literature (including patents) pertaining to electroless plating of metal onto polymer substrates, see the monograph entitled "Plating of Plastics—Recent Developments" by F. A. Domino, Chemical Technology Review No. 138, Noyes Data Corporation, N.J. (1979).

The general method described above has been employed to produce patterns with 150 micron resolution on epoxy substrates (J. K. Dorey, et. al., U.S. Pat. No. 4,537,799; granted Aug. 27, 1985). In a related report, metal lines 100 microns in width were fabricated on a polyphenylene sulfide substrate using a procedure in which laser annealing and chemical doping replaced the development and etching steps. These methods involve a considerable number of steps, making them time-consuming and expensive, especially in comparison to the present invention.

It is known that selective activation of an insulative substrate can be accomplished by using stamps or stencils to deposit an "ink" containing either reducible metal complexes or redox reagents that reduce activating metal ions on the substrate surface to produce a metal plate. The resolution of the metal pattern produced by this method is severely limited by the physical size to which the stamp or stencil can be reduced. This general procedure is employed to produce metal patterns on ceramic substrates. It is known that a reducible metal complex, applied as a mixture with a polymeric binder through a stencil to an alumina substrate, can be transformed to a metal pattern by heat treatment. The drawbacks of this method include limited feature resolution, poor adherence of the metal to the substrate and an expensive firing process.

OBJECTS OF THE INVENTION

In Relation To Printed Circuitry

The principal object of the object of the invention with respect to the technology of printed circuitry is to provide a quick, simple, and inexpensive method of producing conductive pathways on an insulative substrate.

Another object of the invention with respect to the technology of printed circuitry is to provide a method whereby adherent metal patterns can be produced on an insulative substrate.

A further object of the invention with respect to the technology of printed circuitry is to provide a method for the selective deposition of metal on an insulative substrate.

Another object of the invention with respect to the technology of printed circuitry is to provide a method of producing printed circuits utilizes relatively non-hazardous aqueous electroless plating solutions that are commercially available in bulk and are relatively inexpensive.

THE DRAWINGS

FIG. 1A schematically depicts the formation of a covalently-bound, self-assembled organosilane monolayer film on a solid substrate by chemisoption of silane molecules from a homogeneous solution onto the surface of the solid substrate.

FIG. 1B diagramatically defines the symbols used in the drawings.

FIG. 2 schematically depicts the irradiation of a region of the monolayer film to cause the reactive moieties at the upper terminals of the silane molecule to become unreactive.

FIG. 3 schematically depicts the adherence of the colloidal catalytic precursor to the remaining reactive moieties at the upper terminals of the silane molecules.

FIG. 4 schematically depicts the activation by the sensitizing catalytic precursor of the formation of a metal plate on the monolayer film.

FIG. 5 schematically depicts the profile of a semiconductor substrate after an ion etch and shows the metal film on the plateau formed by etching of the substrate.

SUMMARY OF THE INVENTION

In one embodiment of the invention, selective metallization with high resolution on a silicon substrate is achieved by silanizing a silicon wafer to produce a monomolecular silane layer covalently linked to terminal olefin groups at the wafer's surface which are exposed at the interface. Isolated olefins are known to undergo pi* ←pi transitions when irradiated with light having wavelengths lower than 210 nm. Those electronic transitions are used in the invention to produce radicals that initiate polymerization reactions in the thin film. To that end, the wafer's surface may be irradiated with X-rays, electon beams, gamma rays, or with deep ultraviolet light (i.e. UV light with wavelengths below 210 nm) whose intensity and length of irradiation is sufficient to polymerize certain regions of the film. Without subjecting the wafer to an intermediate development step after irradiation, the wafer's surface is then coated with a colloidal platinum-tin (Pd/Sn) catalyst precursor which adheres only to those region of the film that had not been irradiated. Upon subsequent immersion of the wafer in an electroless plating bath, metal is deposited only in those regions activated by the Pd/Sn catalyst.

A principal feature of the invention, as schematically indicated in FIG. 3, is the adherence of the colloidal palladium/tin (Pd/Sn) catalyst precursor to the substrate only in those regions that are to be plated in the electroless bath. Once the catalytic layer is formed in the desired pattern, the remainder of the electroless plating procedure, schematically indicated in FIG. 4, is straightforward. The invention resides in interposing a thin film between the substrate and the catalytic layer in a manner such that the thin film is strongly adherent to the substrate and the catalyst is selectively adherent to a high resolution pattern formed in the film.

There are numerous classes of substances whose molecules, under appropriate conditions, self-assemble to form thin films. In general, those self-assembling molecules characteristically include a polar end, a non-polar opposite end with a reactive moiety at or near the terminus, and an intermediate region typically composed of saturated or unsaturated hydrocarbon chain.

The class of polar end groups (which interact with the polar surface of the substrate) include silanes of the $R_nSiX_m$ type where R is an organic functional group;

n is a number between 1 and 3, i.e. $1 < n < 3$;

$m = 4-n$; and

X is a halogen or alkoxy.

The class of polar end groups further includes carboxylic acids, acid chlorides, anhydrides, sulfonyl groups, phosphoryl groups, hydroxyl and amino acid groups.

The class of non-polar end groups include olefins, acetylenes, diacetylenes, acrylates, methacrylates and esters.

Polar substrates include silica (quartz and glass), alumina, silicon (doped and undoped), other semiconductors (e.g., germanium, gallium arsenide or organic polymers such as epoxy or polysulfone) that either intrinsically possess or are treated to have polar functional groups at the surface, metals, and metal oxides. The bifunctional molecules may be anchored to the substrate by a variety of procedures involving chemical, photochemical, catalytic, or other reactions.

The self-assembling thin film procedure utilized in the invention produces a uniform ultra-thin (>200 nm) monomolecular film having externally accessible reactive groups. Various methods can be employed to alter the reactivity of those groups. The choice of method may be determined in part or in whole by the desired resolution of the pattern to be produced in the film. Among the various methods is the method of making the olefinic groups unreactive or less reactive by polymerization to a saturated structure. As a corollary olefins could be made more reactive to certain coupling agents (such as appropriately modified biomolecules, catalysts, and spectroscopic probes) by oxidation to produce hydroxyl groups. Alteration of reactivity in predetermined regions of the thin film allows chemical reactions to occur either (1) only in those regions whose reactivity has been altered, or (2) everywhere except the altered regions. Consequently, an important attribute of the invention is the ability to produce, with high resolution, sites in the film of different chemical reactivity such that only the reactive moieties are receptive to adhesion by a catalytic precursor to an electroless plating bath.

Where the substrate is a semiconductive wafer of silicon (which can be p-type, n-type, or intrinsic silicon), the film is produced by a monomolecular layer of a silane of the self-assembling kind. Examples of that kind of silane are 7-octenyldimethylcholorosilane and 5-hexenyldimethylchlorosilane. The film is anchored to the silicon substrate by siloxane (Si-0-Si) bridges. Any substrate having a terminal ionizable hydroxyl group at the surface can provide an anchorage for the silane film. This procedure of using self-assembling monolayers involves covalent bond formation between the monolayer and the substrate whereby the film adheres to the substrate more strongly than physisorbed Langmuir-Blodgett films.

Referring now to FIG. 1A, there is schematically shown the formation of a self-assembling monolayer of silane on a solid substrate by adsorption of silane molecules from a silane solution onto the surface of the solid substrate. In that schematic drawing, the silane molecule is represented as having a "polar" head at one end joined by a hydrocarbon chain to a non-polar functional group situated at the other end of the molecule. As schematically indicated in FIG. 1B, where the non-polar functional group has a reactive moiety, that terminal group is symbolized by a triangle; where the terminal group has an unreactive moiety, the group is symbolized by an asterisk.

By irradiating selected regions of the silane monolayer with vacuum-UV light, in the manner indicated in FIG. 2, the reactive moieties at the upper end of the irradiated silane molecule undergo photo-induced polymerization. When the Pd/Sn colloidal catalyst, as schematically indicated in FIG. 3, is spread over the surface of the wafer, the colloidal catalyst binds only to the moieties at the interface that were not irradiated. The catalyst does not adhere to the non-polar groups whose reactive moieties were inactivated by exposure to the vacuum-UV radiation. When the wafer is immersed in an electroless plating bath, plating occurs, as depicted in FIG. 4, only where the Pd/Sn catalyst precursor is adherent to the silane monolayer. On subjecting the metal patterned substrate to an ion etch, metal topped plateaus remain after the etch, as schematically depicted in FIG. 5.

EXAMPLE 1

An n-type silicon wafer (obtained from Monsanto, St. Louis, Mo.) having a native oxide surface was cleaned by standard techniques. After cleaning, wettability of the surface by triply-distilled water was determined, using a Zisman type contact angle goniometer, to be 0°, indicative of an extremely hydrophilic surface (i.e. the surface was wet by the water which spread and formed a film upon the surface). A 1% (v/v) solution of 7-octenyldimethylcholorosilane (ODMC: Petrarch Co., Bristol Pa.) in toluene at room temperature was applied to the surface of the silicon wafer for a time (e.g., 15 minutes) sufficient to enable a monomolecular film of the ODMC to be chemisorbed onto the silicon. Residual solvent was removed from the film by baking the wafer on a hot plate for 5 minutes in air at a temperature of about 100° C. The silanized surface was very hydrophobic (i.e. repellant to water), giving a contact angle with water of 85°.

XD2408 palladium chloride/tin chloride colloidal activator (MacDermid Co., Waterbury, Conn.) was used as received. The silanized wafer surface was covered by the Pd/Sn colloidal activator for five minutes. The wafer was then rinsed copiously with water. The surface of the wafer was clearly hydrophilic, indicative of the bonding of the colloid. The wafer was then immersed for five minutes in a Metex 9027 electroless copper plating bath prepared in accordance with the manufacturer's (MacDermid) directions. The wafer, after removal from the bath, was thoroughly rinsed with water. A copper metal coat was visible over the surface of the wafer. Examination of the surface of the wafer using a scanning electron microscope revealed the presence of a uniform, continuous metal coat on the wafers' surface.

EXAMPLE 2

The entire procedure specified in Example 1, except for the omission of the step of silanizing the surface of the wafer with ODMC and an increase of the time in the plating bath was repeated using a similar n-type silicon wafer with a native oxide surface (obtained from Monsanto). After 15 minutes immersion in the electroless copper plating bath only a few small, randomly distributed patches of metal were present on the wafer surface.

EXAMPLE 3

An n-type silicon wafer with a native oxide surface (obtained from Monsanto) was silanized using the procedure described in Example 1. The wafer was then placed in an argon atmosphere and irradiated for 10 minutes with ultraviolet light from a Mercury/Argon lamp (Oriel Co., Stamford Conn.) that was spaced at a distance of 3 cm from the wafer. The intensity of the radiation, as measured with a Mamir UV dosimeter at 254 nm was 4.3 mw/cm$^2$ at 3 cm from the irradiated surface of the wafer. After being immersed for 15 minutes in the copper plating bath employed in Example 1, no copper plate was present on the wafer.

EXAMPLE 4

An n-type silicon wafer with a native oxide surface (obtained from Monsanto) was cleaned by standard techniques and was then silanized using the procedure described in Example 1. After the residual solvent had been driven off the wafer was allowed to cool to room temperature. A low resolution metal mask was placed upon the silanized surface to block the light in selected regions. The wafer was then flood irradiated for 10 minutes by ultra violet (UV) light from a mercury/argon (Hg/Ar) lamp (Oriel Co, Stamford, Conn.) while the wafer was situated in an inert gaseous atmosphere of argon. The intensity of the UV radiation, as measured with a Mamir UV dosimeter, was 4.3 m V/cm$^2$ at 3 cvm from the surface of the wafer and the measured wavelength of that UV radiation was 254 nm. After exposure to the UV radiation, the wafer surface was immersed in the XD2408 palladium chloride/tin chloride colloidal activator (MacDermid & Co.) for five minutes. The wafer was then thoroughly rinsed with water. Only the regions of the surface that had not been irradiated were hydrophobic. That result indicated that the olefinic silane interacted strongly with the Pd/Sn colloid. Subsequent immersion of the wafer into the Metex 9027 Cu bath for five minutes, as in Example 1, produced a thin copper plate that reproduced the features of the masked regions.

EXAMPLE 5

An n-type silicon wafer with a native oxide surface (obtained form Monsanto) was silanized using the Example 1 procedure except that a 2% (V/V) solution of the ODMC silane in toluene was used. The silanized wafer was irradiated for 15 minutes through a photolithograph mask having an electron beam defined chrome film on a quartz blank. Prior to silanization of the wafer, a Pd/Sn colloidal activator had been prepared from Cataposit 44 concentrate and solid Cataprep 404, as directed by the manufacturer (Shipley Company, Newton, Mass.). An electroless copper plating bath had also been prepared from 328A and 328Q stock solutions as prescribed by the Shipley Company which manufactured those stock solutions.

After irradiation, using the photolithography procedure, the wafer was covered by the Shipley colloid for five minutes. After a thorough rinse with distilled water, the wafer was immersed in the copper plating bath for two and one half minutes. After rinsing the wafer, the wafer surface was inspected by bright field reflectance microscopy. That inspection showed that the pattern of the mask had been reproduced in copper on the wafer. The thickness of the copper film, measured with a Sloan Dektak profilometer, was 20 nm. The conductivity of the film was 5000 mho/cm as measured with a two-point probe apparatus.

The copper patterned wafer was placed in a Plasmatherm Model 54 reactive ion etch system (Plasmatherm Co., Crescent, N.J.) and exposed to CF$_4$+ plasma for five minutes. Under the prevailing conditions, the etch rate of silicon was 0.1 microns/min, giving a total etch of 0.5 microns. Examination of the wafer with a Nikon Optiphot M differential interference contrast Nomarski microscope revealed that the wafer had been etched to a depth of 0.5 microns everywhere except beneath the copper plating. Lines five microns in width with five micron spacing between adjacent lines (the resolution of the edges was about 1 micron), as well as other patterns, had been reproduced on the silicon wafer as raised regions above the etched surface, i.e. as plateau regions. It was evident that the copper pattern had served as a high resolution, positive resist layer. Examination of the etched wafer by X-ray fluorescence line scan in a ISI Scanning Electron Microscope equipped with a Kevex energy-despersive, X-ray spectrometer, showed that copper was still present in the raised areas and proved that the copper plate had survived five minutes in the ion plasma.

EXAMPLE 6

A copper patterned n-type silicon wafer was produced using the Example 5 procedure. However, a different photolithograph chrome on quartz mask having sub-micron features was employed for patterning. Before subjecting the copper patterned silicon wafer to the CF$_4$+ plasma etch, a microscopic examination of the wafer revealed excellent reproduction of the mask pattern in copper on the surface of the wafer. After plasma etching the wafer for five minutes, the wafer was removed from the etching apparatus and was then examined with an electron microscope. The resistance of the copper plate to the plasma etch was apparent in the metallized regions where copper of approximately 40 nm thickness remained in the raised regions. Among the features reproduced on the wafer were lines about one centimeter long and less than 2 microns wide, lines 4 microns long and about a half micron in width, and a square cavity (i.e. a "trough") about five microns on a side.

EXAMPLE 7

The procedure of Example 4 was repeated using a p-type silicon wafer (obtained from Monsanto). As in Example 4, a thin copper plate was formed on the wafer that reproduced the features of the masked regions. No appreciable difference was discerned between the plate on the p-type wafer and the plate on the n-type wafer.

EXAMPLE 8

The procedure of Example 1 was repeated using a 1% solution of 5-hexenyldimethylchlorosilane (HDMC; Petrarch Co., Bristol, Pa.) in toluene. The wafer was irradiated and then plated with copper as in example 5. There was no apparent difference between the metal pattern produced on the HDMC-treated surface and the ODMC-treated surface.

Conclusion

Obvious modifications that do not depart from the essentials of the invention are apparent to those skilled in semiconductor fabrication or in printed circuitry or in the chemistry of thin films. In view of the changes in the invention that are obvious to such skilled persons, it is intended that the invention not be limited to the precise procedures here described not to the specific materials used in those procedures. Rather, it is intended that the scope of the invention be construed in accordance with the accompanying claims, having due consideration for changes that merely involve obvious equivalents and for the substitution of materials having known similar properties.

We claim:

1. A process for producing conductive paths on a substrate of the kind having polar functional groups at its surface, comprising the steps of;
   (a) causing a self-assembling monomolecular film to be chemically adsorbed on the surface of the substrate,
   (b) altering the reactivity in regions of the film to produce a predetermined pattern in the film,
   (c) causing a catalytic precursor to adhere only to those regions of the film that have sufficient reactivity to bind the catalytic precursor, and
   (d) placing the wafer in an electroless metal plating bath whereby a metal plate is produced in those regions having the catalytic precursor thereon.

2. The process according to claim 1 wherein the substrate is a semiconductor substance and wherein the self-assembling monomolecular film is a silane of the $R_nSiX_m$ type where;

R is an organic functional group;
   $1 < n < 3$;
   $m = 4-n$; and
   X is a halogen or alkoxy.

3. The process according to claim 1, wherein the substrate is a solid of semiconductive silicon and wherein the self-assembling monomolecular film is produced on the solid by adsorption from a solution containing a chlorosilane.

4. The process according to claim 3, wherein the chlorosilane in solution is 7-octenyldimethylchlorosilane.

5. The process according to claim 3, wherein the chlorosilane in solution is 5-hexenyldimethylchlorosilane.

6. The process according to claim 2, wherein the catalytic precursor is a colloid containing palladium and tin.

7. The process according to claim 6, wherein the palladium and tin in the colloid are in chemical compounds of those metals.

8. The process according to claim 1, wherein the reactivity in regions of the film is altered by irradiating those regions with irradiation that promotes polymerization of the irradiated regions.

9. The process according to claim 8, wherein the wafer is situated in a vacuum or an inert atmosphere during the irradiation procedure.

10. The process according to claim 9, wherein the irradiation is UV light whose wavelength is less than 200 nm.

11. The process according to claim 10, wherein the self-assembling film is a silane layer.

12. The process according to claim 1, wherein the substrate is a solid of semiconductive silicon having hydroxyl groups on its surface and wherein the self-assembling monomolecular film is bound to the substrate by siloxane bridges to those hydroxyl groups.

* * * * *